US00PP34731P2

(12) United States Plant Patent
Danziger

(10) Patent No.: US PP34,731 P2
(45) Date of Patent: Nov. 8, 2022

(54) ***SALVIA* PLANT NAMED 'DSALDRKMTR'**

(50) Latin Name: *Salvia nemorosa*
Varietal Denomination: DSALDRKMTR

(71) Applicant: Danziger 'DAN 'Flower Farm, Beit Dagan (IL)

(72) Inventor: Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

(21) Appl. No.: 17/577,436

(22) Filed: Jan. 18, 2022

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475, 226

CPC ... A01H 5/02; A01H 5/12; A01H 5/00; A01H 6/50; A01H 6/508; A61K 36/537
See application file for complete search history.

(56) References Cited

PUBLICATIONS

Floral Daily 2021 Danziger kicks of the 2022 season with NovemberFest, retrieved on Mar. 8, 2022, retrieved from the Internet at https://www.floraldaily.com/article/9286013/danziger-kicks-off-the-2022-season-with-novemberfest/, 9 pp. (Year: 2021).*
Germania Seed Company Mast Young Plants 2022, retrieved on Mar. 8, 2022, retrieved from the Internet at https://germaniaseed.com/orderforms/2022/mast_741_2022.pdf pp. 1-3, 21. (Year: 2021).*

* cited by examiner

*Primary Examiner* — June Hwu
(74) *Attorney, Agent, or Firm* — Cassandra Bright

(57) ABSTRACT

A new and distinct cultivar of *Salvia* plant named 'DSALDRKMTR' is disclosed, characterized by large, dark blue flowers. The new variety is a *Salvia*, normally produced as an outdoor garden or container plant.

2 Drawing Sheets

Latin name of the genus and species: *Salvia nemorosa*.
Variety denomination: 'DSALDRKMTR'.

BACKGROUND OF THE INVENTION

The new *Salvia* cultivar is the product of a planned breeding program conducted by the inventor, Gavriel Danziger, in Moshav Mishmar Hashiva, Israel. The objective of the breeding program was to produce new *Salvia* varieties for ornamental commercial applications. The open pollination resulting in this new variety was made in 2017.

The seed parent is an unpatented, unnamed proprietary *Salvia nemerosa* 'SAN-13-2959'. The pollen parent is unknown as it was an open pollination breeding program. The new variety was discovered in May 2018 by the inventor in a group of seedlings resulting from the 2017 open pollination, in a research greenhouse in Moshav Mishmar Hashiva, Israel.

Asexual reproduction of the new cultivar was performed by terminal vegetative cuttings. This was first performed at a research greenhouse in Moshav Mishmar Hashiva, Israel in September 2018, and has shown that the unique features of this cultivar are stable and reproduced true to type in multiple successive generations.

SUMMARY OF THE INVENTION

The cultivar 'DSALDRKMTR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DSALDRKMTR' These characteristics in combination distinguish 'DSALDRKMTR' as a new and distinct *Salvia* cultivar:

1. Large flowers.
2. Dark blue flowers.

PARENTAL COMPARISON

Plants of the new cultivar 'DSALDRKMTR' are similar to plants of the seed parent, in most horticultural characteristics, however, plants of the new cultivar 'DSALDRKMTR' differ in the following:

1. Leaves of the new variety are entire; leaves of the seed parent are lobed.
2. Flower color of the new variety is a darker blue than the flower color of the seed parent.

COMMERCIAL COMPARISON

Plants of the new cultivar 'DSALDRKMTR' are comparable to the commercial variety *Salvia* 'DSALAXBL', U.S. Plant Pat. No. 32,919. The two *Salvia* varieties are similar in most horticultural characteristics; however, the new variety 'DSALDRKMTR' differs in the following:

1. Flowers of the new variety are larger than the flowers of this comparator.
2. Leaves of the new variety are larger than leaves of this comparator.

Plants of the new cultivar 'DSALDRKMTR' can also be comparable to the commercial variety *Salvia*

'DSALRS203', U.S. Plant Pat. No. 26,520. The two *Salvia* varieties are similar in most horticultural characteristics; however, the new variety 'DSALDRKMTR' differs in the following:

1. Flower color of the new variety is a darker blue than the flower color of this comparator.
2. Leaves of the new variety are smaller than the leaves of this comparator.

BRIEF DESCRIPTION OF THE PHOTOGRAPHS

Figure 1:
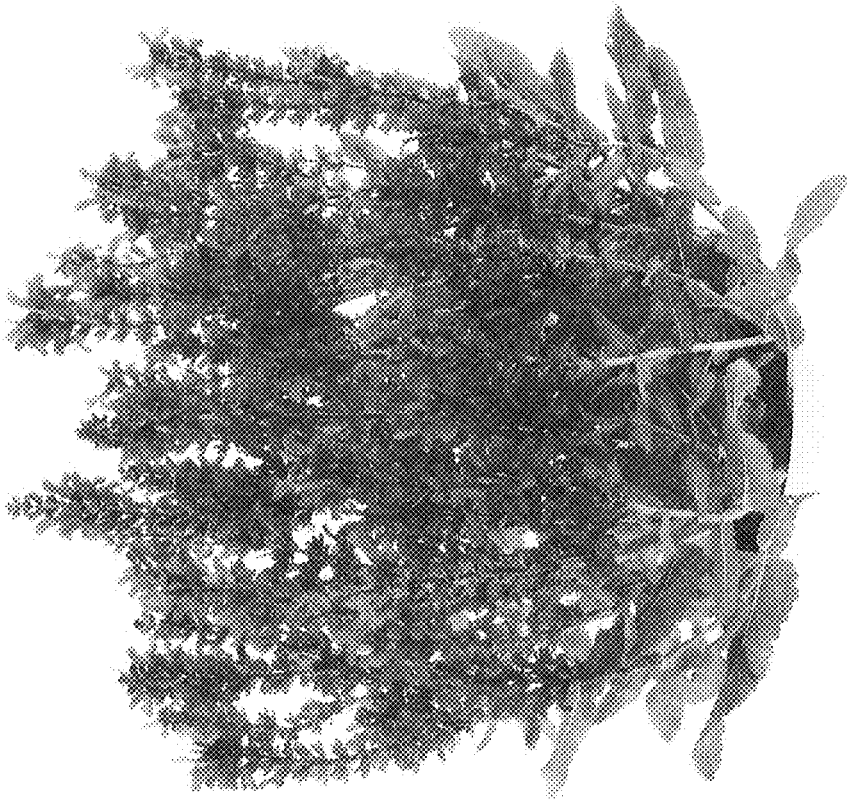

The accompanying photograph in FIG. 1 illustrates in full color a typical plant of 'DSALDRKMTR' grown in 25 cm pot outdoors in Moshav Mishmar Hashiva, Israel.

Figure 2:
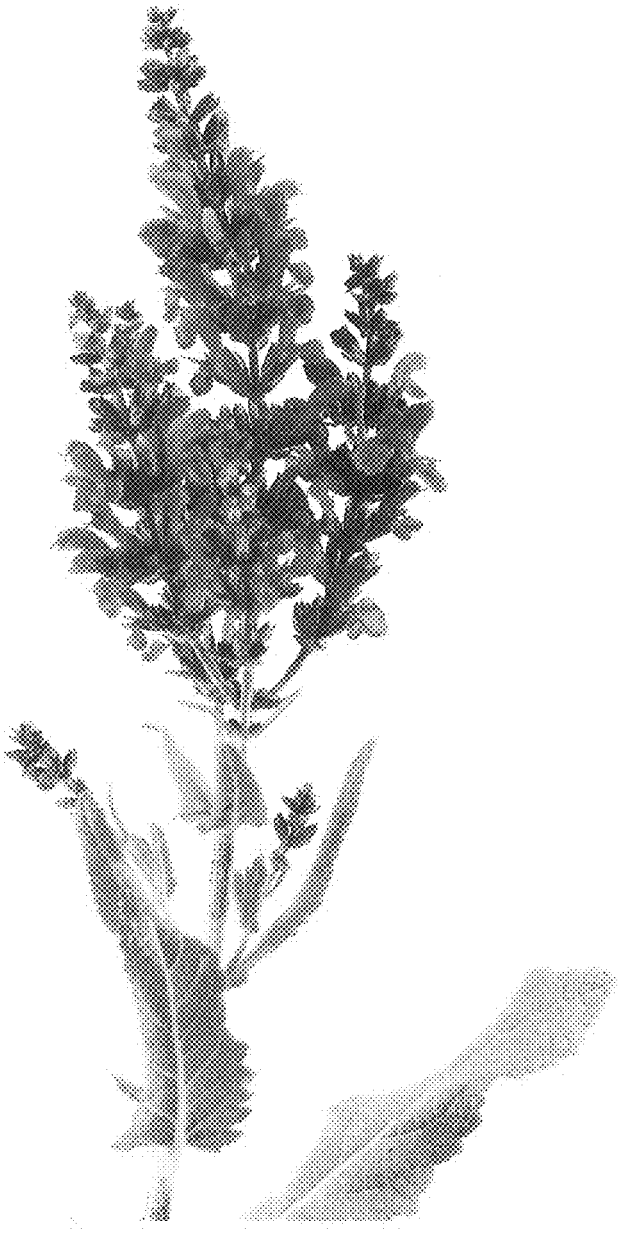

FIG. 2 illustrates a close up of the inflorescence. Age of the plant photographed is approximately 6 months from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005, except where general terms of ordinary dictionary significance are used. The following observations and measurements describe 'DSALDRKMTR' plants grown from autumn to spring in moderate climate in a greenhouse, in Moshav Mishmar Hashiva, Israel. General light conditions are bright, normal sunlight. Measurements and numerical values represent averages of typical plant types.

Botanical classification: *Salvia nemerosa* 'DSALDRKMTR'.

PROPAGATION

Type of propagation typically used: Vegetative cuttings.

Time to initiate roots: 5 to 7 days at approximately 18-24° C.

Time to produce a rooted cutting: About 10 to14 days at 18-24° C.

Root description: Moderately dense and fibrous. Medium brown in color, not accurately measured with R.H.S. chart.

PLANT

Overall plant shape or growth habit: Compact, spreading and upright.

Plant spread: Approximately 30 to 35 cm.

Plant height: Approximately 30 to 35 cm.

Growth rate: Moderate to fast.

Length of primary lateral branches: Approximately 30 to 35 cm.

Diameter of lateral branches: Approximately 0.5 cm.

Quantity of lateral branches: About 8.

- *Color*.—Near RHS Yellow-Green 144B.
- *Texture/pubescence*.—Silky and smooth, velvet like short hairs, stems are slightly ribbed lengthwise.

Internode length: Approximately 3 to 4 cm.

Age of plant described: Approximately 12 weeks from a rooted cutting.

FOLIAGE

Leaf:

- *Arrangement*.—Opposite.
- *Quantity*.—Approximately 8 to 10 per main branch.
- *Average length*.—Approximately 3.5 to 11 cm.
- *Average width*.—Approximately 1 to 5 cm.
- *Shape of blade*.—Ovate.
- *Apex*.—Apiculate.
- *Base*.—Obtuse.
- *Attachment*.—Petiolate.
- *Margin*.—Crenate. Shallow crenations.
- *Texture of top surface*.—Bullate.
- *Texture of bottom surface*.—Glabrous.
- *Color*.—Young foliage upper side: Near RHS Yellow-Green 143A. Young foliage under side: Near RHS Yellow-Green 143B. Mature foliage upper side: Near RHS Green N137A. Mature foliage under side: Near RHS Green N137C.
- *Venation*.—Type: Anastomosing. Venation Color, Upper Side: Near RHS Yellow-Green 147C. Venation Color, Under Side: Near RHS Yellow-Green 147C.
- *Petiole*.—Average Length: Approximately 0.5 to 4 cm. Diameter: Approximately 0.15 cm. Color: Near RHS Yellow-Green 147C.
- *Leaf fragrance*.—None detected.

FLOWER

Natural flowering season: Under moderate climate such as in Israel — from end of winter to late fall (February-November). Under cooler weather condition will flower from April to September.

Inflorescence type and habit: Verticil, upright habit.

Flower longevity on plant: About 5 to 7 days.

Quantity of flowers: About 56 blooming spikes per plant.

Inflorescence size:

- *Diameter*.—Approximately 2 cm.
- *Height*.—Approximately 9 to 17 cm.

Inflorescence:

- *Flowers and buds per inflorescence*.—Approximately 50 to 70.
- *Inflorescence internode*.—Medium to long.
- *Florets per inflorescence node/branchlet*.—Average range 15 to 20 flowers per inflorescence branchlet.
- *Inflorescence tip attitude*.—Erect with a slight curve.
- *Inflorescence bract*.—Length: 10 to 18 mm. Color: Near RHS 138A. Persistence: Persistent, drying slightly with maturity.

Peduncle:

- *Length*.—3 to 5 cm.
- *Diameter*.—0.2 cm.
- *Texture*.—Lightly pubescent with soft, short feather-like hairs, slightly ribbed.
- *Color*.—Near RHS Yellow-Green 146B.
- *Orientation*.—Upright.
- *Strength*.—Strong and flexible.

Individual flowers:

- *Diameter*.—Approximately 0.4 cm.
- *Length*.—Approximately 2 cm.
- *Persistence*.—Non-persistent.
- *Fragrance*.—Delicate, sage-like.

Petals:

*Petal arrangement*.—The corolla is sympetalous and typically bilabiate with 2 small, highly fused lobes forming an upper lip and 3 larger highly fused lobes forming a lower lip.

*Margin*.—Entire.

*Tip shape*.—Upper Lip: Rounded. Lower Lip: Blunt.

*Length*.—Upper Lip: 1 cm. Lower Lip: 0.5 cm. Tube: 1 cm.

*Width*.—Upper Lip: 0.3 cm. Lower Lip: 0.3 cm. Tube: 0.5 cm.

*Texture*.—Upper Lip: Smooth, slightly pubescent, matte. Lower Lip: Smooth. Tube: Smooth, slightly ribbed lengthwise.

*Color*.—Upper Lip: When Opening: Inner Surface: Near RHS Violet 91A. Outer Surface: Near RHS Violet-Blue N89B. Fully Opened: Inner Surface: Near RHS Violet 91A. Outer Surface: Near RHS Violet-Blue N89B. Fading: Inner Surface: Near RHS Violet 91A. Outer Surface: Near RHS Violet 92A. Lower Lip: When Opening: Inner Surface: Near RHS Violet-Blue N89B. Outer Surface: Near RHS Violet-Blue N89B. Fully Opened: Inner Surface: Near RHS Violet-Blue N89B. Outer Surface: Near RHS Violet-Blue N89B. Fading: Inner Surface: Near RHS Violet 92A. Outer Surface: Near RHS Violet 92A. Tube: When Opening: Inner Surface: Near RHS Purple 85D. Outer Surface: Near RHS Purple 85D. Fully Opened: Inner Surface: Near RHS Purple 85D. Outer Surface: Near RHS Purple 85D. Fading: Inner Surface: Near RHS Purple 85D. Outer Surface: Near RHS Purple 85D.

Bud:

*Shape*.—Ovate.

*Length*.—0.8 cm.

*Diameter*.—0.3 cm.

*Color*.—Near RHS Violet-Blue N89A.

Sepals:

*Shape*.—Fused at base to form a tube.

*Quantity*.—3 per flower.

*Length*.—Approximately 0.7 cm.

*Width*.—Approximately 0.4 cm.

*Margin*.—Entire.

*Texture*.—Lightly pubescent with soft, short feathers like hairs.

*Color*.—RHS Red-Purple N77A mixed with Green N137A.

REPRODUCTIVE ORGANS

Stamens:

*Number*.—2.

*Filament length*.—Approximately 1 cm.

Anthers:

*Shape*.—Oblong.

*Length*.—Approximately 0.15 cm.

*Color*.—RHS Purple 79B.

*Pollen*.—Medium amount.

Pistil:

*Number*.—1.

*Length*.—Approximately 1.3 cm.

*Style*.—Length: Approximately 1 cm. Color: RHS Purple 79B.

*Stigma*.—Shape: V-shaped. Color: Near RHS Violet-Blue N88A. Ovary Color: Near RHS Yellow-Green 146C.

OTHER CHARACTERISTICS

Seeds and fruits: Up to four per flower, colored near RHS Brown Group N200A.

Disease/pest resistance: Neither resistance nor susceptibility to normal diseases and pests of *Salvia* has been observed.

Temperature tolerance: USDA Zones 4-9.

Drought tolerance: Not tolerant to drought.

What is claimed is:

1. A new and distinct cultivar of *Salvia* plant named 'DSALDRKMTR' as herein illustrated and described.

* * * * *